US007022785B2

(12) United States Patent
Winslow

(10) Patent No.: US 7,022,785 B2
(45) Date of Patent: Apr. 4, 2006

(54) DIIMINE COMPLEXES FOR OLEFIN POLYMERIZATION

(75) Inventor: Linda N. Winslow, Cincinnati, OH (US)

(73) Assignee: Equistar Chemicals L.P., Houston, TX (US)

( * ) Notice: Subject to any disclaimer, the term of this patent is extended or adjusted under 35 U.S.C. 154(b) by 334 days.

(21) Appl. No.: 10/087,028

(22) Filed: Mar. 1, 2002

(65) Prior Publication Data

US 2003/0166805 A1    Sep. 4, 2003

(51) Int. Cl.
*C08F 4/44* (2006.01)
*B01J 31/38* (2006.01)

(52) U.S. Cl. ............ 526/171; 526/172; 526/348; 502/155; 502/167

(58) Field of Classification Search ......... 526/171, 526/172, 348; 502/155, 167
See application file for complete search history.

(56) References Cited

U.S. PATENT DOCUMENTS 5,880,241 A * 3/1999 Brookhart et al. .......... 526/348

FOREIGN PATENT DOCUMENTS

WO    WO 01/92342 A2    6/2001

WO    WO 01/92432 A2 * 12/2001

OTHER PUBLICATIONS

Thomas Schleis et al., "Ni(II) and Pd(II) Complexes of Camphor-derived Diazadiene Ligands: Steric Bulk Tuning and Ethylene Polymerization," Inorganic Chemistry Communications, 1 (1998), 431-434.

Peter Belser et al., "Syntheses and Properties of Ruthenium (II) Complexes with o-Quinodiimine Ligands. Crystal and Molecular Structure of $Ru(bpy)_2(C_6H_4(NH)_2)(PF_6)_2$," Inorg. Chem., 1981, 20, 3098-3103.

A. Alousy et al., "Solvatochromism and Piezochromism of Dicyana-, Tricyanao-, and Tetracyano-diimine-iron(II) Complexes," Transition Metal Chemistry, 27: 244-252, 2002.

* cited by examiner

*Primary Examiner*—Robert D. Harlan
(74) *Attorney, Agent, or Firm*—Brooks Kushman P.C.

(57) ABSTRACT

The present invention provides a catalyst comprising a diimine complex coordinated a transition metal. The complex includes a Group 3 to 10 transition or lanthanide metal and one or more anionic or neutral ligands in an amount that satisfies the valency of the metal such that the complex has a net zero charge. The present invention also discloses a method for coupling olefins utilizing the catalyst of the present invention.

20 Claims, No Drawings

DIIMINE COMPLEXES FOR OLEFIN POLYMERIZATION

BACKGROUND OF THE INVENTION

1. Field of the Invention

This invention relates to transition metal diimine complexes, and in particular, to transition metal diimine complexes useful for olefin coupling and polymerization.

2. Background Art

The chemical industry uses a wide variety of transition metal complexes as catalysts for organic reactions. Olefin polymerization is an important example of such a reaction. While conventional Ziegler-Natta catalysts continue to dominate the industry, highly active metallocene or single-site catalysts that give new polymers with narrow molecular weight distributions, low densities, and good comonomer incorporation are emerging.

Transition metal complexes used to polymerize olefins are normally non-zero-valent metals (e.g., $Ti^{4+}$, $Zr^{4+}$, $Sc^{3+}$) surrounded by anionic ligands (e.g., chloride, alkyl, cyclopentadienyl) that satisfy the valency of the metal. Anionic ligands can dramatically affect catalyst activity and polymer properties. Thus, a catalyst structure can be fine-tuned to give polymers with desirable properties. Furthermore, the anionic ligand will affect the stability of the transition metal complexes.

Metallocene polymerization catalysts contain one or two cyclopentadienyl groups as anionic ligands. These serve to stabilize the active catalytic species, modulate the electronic and steric environment around the active metal center, and maintain the single-sited nature of the catalyst. Polymers with narrow molecular weight and composition distributions are formed from these metallocene catalysts. Such complexes frequently contain substituted cyclopentadienyl groups. Substituents on the cyclopentadienyl ring may change the geometry and electronic character of the active site.

Another class of anionic ligands includes cyclic, heteroatom-containing ligands which are isolobal to the cyclopentadienyl ring; that is, the orbital interaction of the metal with the ligand is similar in both cases. Examples of such ligands are boraaryl (see, e.g., U.S. Pat. No. 5,554,775), pyrrolyl and indolyl anions (U.S. Pat. No. 5,539,124), azaborolinyl groups (U.S. Pat. No. 5,902,866), phospholyl anions, and tris(pyrazolyl)borate anions.

Ruthenium complexes which include o-quinodiimine ligands have been reported by P. Belser et al, *Inorg. Chem.* 20, p. 3098 (1981). However, the utility of aryl diimine transition metal compounds such as o-quinodiimine and 9,10-phenanthrenequinone diimine transition metal complexes as olefin polymerization catalysts has not been described.

SUMMARY OF THE INVENTION

In one embodiment of the present invention, a transition metal catalyst comprising a diimine ligand coordinated to a transition metal is provided. The structure of the diimine ligand coordinated to a transition metal of the present invention is given by:

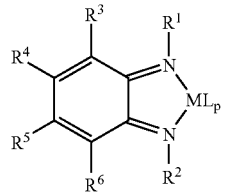

I where M is preferably a metal selected from Groups 3 to 10 of the Periodic Table, more preferably M is a metal selected from Groups 8 to 10 of the Periodic Table, and most preferably M is nickel, palladium, iron, or cobalt; $R^1$ and $R^2$ are the same or different and are independently selected from hydrogen, a $C_{1-10}$ alkyl group, a $C_{6-10}$ aryl group, or a $C_{7-15}$ aralkyl group each of these groups optionally substituted with a halogen, a cyano group, a $C_{1-4}$ alkoxy group, or a $C_{1-4}$ alkyl group, and with the proviso that not more than 1 of $R^1$ or $R^2$ is a hydrocarbon which is branched at the imino-bonded carbon atom; $R^3$, $R^4$, $R^5$, and $R^6$ are independently hydrogen, a $C_{1-10}$ alkyl group, a $C_{6-10}$ aryl group, a $C_{7-15}$ aralkyl group, $C_{1-10}$ alkoxy, or $C_{1-10}$ dialkylamino group, each of these groups optionally substituted with a halogen, a cyano group, a $C_{1-4}$ alkoxy group, or a $C_{1-4}$ alkyl group, or wherein any two adjacent $R^3$ through $R^6$ form a cyclic structure or are part of a larger ring structure, said cyclic structure and said larger ring structure optionally containing one or more heteroatoms, preferably B, N, O, S, or P; L is a neutral or charged ligand; and p is a integer such that complex I is neutral and the valency of M is satisfied. When adjacent $R^3$ through $R^6$ substituents form a ring or ring system, the various rings may be saturated, unsaturated, or aromatic. The rings are preferably $C_5$ or $C_6$ rings. Preferably, $R^1$ and $R^2$ are hydrogen or an unbranched alkyl or alkaryl group.

As examples of a catalyst wherein adjacent $R^3$ through $R^6$ constitute a ring system are transition metal catalysts comprising diimine complexes coordinated to a transition metal given by formula II:

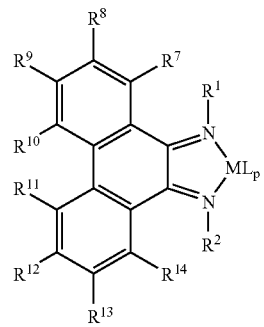

II where M, $R^1$, $R^2$, L, and p are defined above; and $R^7$, $R^8$, $R^9$, $R^{10}$, $R^{11}$, $R^{12}$, $R^{13}$, and $R^{14}$ are independently hydrogen, a $C_{1-10}$ alkyl group, a $C_{6-10}$ aryl group, a $C_{7-15}$ aralkyl group, $C_{1-10}$ alkoxy, or $C_{1-10}$ dialkylamino group, each of these groups optionally substituted with a halogen, a cyano group, a $C_{1-4}$ alkoxy group, or a $C_{1-4}$ alkyl group, or wherein any two of $R^7$ through $R^{14}$, or $R^{10}$ and $R^{11}$ form a cyclic structure or are part of a larger ring structure, said cyclic structure and said larger ring structure optionally containing one or more heteroatoms, preferably B, N, O, S, or P. As is the case with catalysts of the structure of Formula I, additional fused rings may be saturated, unsaturated, or aromatic, and are preferably 5 or 6 membered rings.

In still another embodiment of the present invention, a process for coupling two or more olefins is provided. Such a process includes dimerization, oligomerization, and polymerization. In the processes of the present invention, the complexes described by structures I and II are used to couple olefins.

DETAILED DESCRIPTION OF THE PREFERRED EMBODIMENTS

Reference will now be made in detail to presently preferred compositions or embodiments and methods of the invention, which constitute the best modes of practicing the invention presently known to the inventor.

In one embodiment of the present invention, a transition metal catalyst comprising a diimine complex coordinated to a transition metal given by structure I is provided:

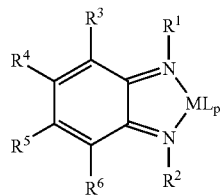

where M is preferably a metal selected from Groups 3 to 10 of the Periodic Table, more preferably M is a metal selected from Groups 8 to 10 of the Periodic Table, and most preferably M is nickel, palladium, iron, or cobalt; $R^1$ and $R^2$ are the same or different and are independently selected from hydrogen, a $C_{1-10}$ alkyl group, a $C_{6-10}$ aryl group, or a $C_{7-15}$ aralkyl group each of these groups optionally substituted with a halogen, a cyano group, a $C_{1-4}$ alkoxy group, or a $C_{1-4}$ alkyl group, and with the proviso that not more than 1 of $R^1$ or $R^2$ is a hydrocarbon which is branched at the imino-bonded carbon atom; $R^3$, $R^4$, $R^5$, and $R^6$ are independently hydrogen, a $C_{1-10}$ alkyl group, a $C_{6-10}$ aryl group, a $C_{7-15}$ aralkyl group, $C_{1-10}$ alkoxy, or $C_{1-10}$ dialkylamino group, each of these groups optionally substituted with a halogen, a cyano group, a $C_{1-4}$ alkoxy group, or a $C_{1-4}$ alkyl group; or wherein any two adjacent $R^3$ through $R^6$ form a cyclic structure or are part of a larger ring structure, said cyclic structure and said larger ring structure optionally containing one or more heteroatoms, preferably B, N, O, S, or P; L is a neutral or charged ligand; and p is a integer such that complex I is neutral and the valency of M is satisfied. When adjacent $R^3$ through $R^6$ substituents form a ring or ring system, the various rings may be saturated, unsaturated, or aromatic. The rings are preferably $C_5$ or $C_6$ rings. Preferably, $R^1$ and $R^2$ are hydrogen or an unbranched alkyl or alkaryl group.

In another embodiment of the present invention, a catalyst comprising a diimine complex coordinated a transition metal given by formula II is provided:

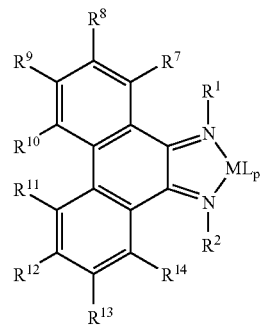

where M, $R^1$, $R^2$, L, and p are defined above; and $R^7$, $R^8$, $R^9$, $R^{10}$, $R^{11}$, $R^{12}$, $R^{13}$, and $R^{14}$ are independently hydrogen, a $C_{1-10}$ alkyl group, a $C_{6-10}$ aryl group, a $C_{7-15}$ aralkyl group, $C_{1-10}$ alkoxy, or $C_{1-10}$ dialkylamino group, each of these groups optionally substituted with a halogen, a cyano group, a $C_{1-4}$ alkoxy group, or a $C_{1-4}$ alkyl group, or wherein any two of $R^7$ through $R^{14}$, or $R^{10}$ and $R^{11}$ form a cyclic structure or are part of a larger ring structure, said cyclic structure and said larger ring structure optionally containing one or more heteroatoms, preferably B, N, O, S, or P. As is the case with catalysts of the structure of Formula I, additional fused rings may be saturated, unsaturated, or aromatic, and are preferably 5 or 6 membered rings.

The one or more anionic or neutral ligands, L, are present in an amount such that the valency of M is satisfied. Examples include unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, boraaryl groups, or the like, and combinations of these. Examples of neutral ligands are carbonyl, $\eta^6$-aryl, $\eta^4$-butadiene, $\eta^4$-cyclobutadiene, $\eta^4$-cyclooctatetraene, tertiary phosphine, and the like. Other examples of suitable anionic or neutral ligands appear in U.S. Pat. Nos. 5,756,611, 5,637,659, 5,637,660, 5,554,775, and 5,539,124, the teachings of which are incorporated herein by reference.

In another embodiment of the invention, the transition metal complex of the present invention further comprises an activator. Generally, the activator converts the complex to a cationically active species. The catalysts are especially valuable for polymerizing olefins, such as ethylene, propylene, and/or other α-olefins such as 1-butene or 1-hexene. Suitable activators are well known in the art. Preferred activators include alumoxanes (i.e., methyl alumoxane, and so-called modified methylalumoxanes, ethyl alumoxane, and diisobutyl alumoxane, alkylaluminum compounds, i.e. triethylaluminum, diethylaluminum chloride, and trimethylaluminum, and the like. Such activators are generally used in an amount within the range of about 0.01 to about 100,000, preferably from about 1 to about 10,000, moles per mole of transition metal complex. Preferred activators also include acid salts that contain non-nucleophilic anions. These compounds generally consist of bulky ligands attached to boron or aluminum. Examples include lithium tetrakis(pentafluorophenyl) borate, lithium tetrakis(pentafluorophenyl) aluminate, anilinium tetrakis(pentafluorophenyl) borate, and the like. These activators are generally used in an amount within the range of about 0.01 to about 1000, preferably from about 1 to about 10, moles per mole of transition metal complex. Suitable activators also include trialkyl or triarylboron compounds such as tris(pentafluorophenyl)boron, tris(pentabromophenyl) boron, and the like. Other suitable activators are described, for example, in U.S. Pat. Nos. 5,756,611, 5,064,802, and 5,599,761, the teachings of which are incorporated herein by reference.

The catalysts are optionally used with an inorganic solid or organic polymer support. Suitable supports include silica, alumina, silica-aluminas, magnesia, titania, clays, zeolites, or the like. The supports can be pretreated thermally or chemically to improve catalyst productivity or product properties. The catalysts can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst. The ligand can also be chemically tethered to the support through a suitable linking group.

In still another embodiment of the present invention, a process for coupling two or more olefins is provided. Such coupling processes include but are not limited to dimerization, oligomerization, and polymerization. In the coupling processes of the present invention, the complexes described by structures I and II are used as catalysts. The process of the present invention comprises:

1) mixing in a reaction vessel a solvent, an activator and a catalyst given by formula I or formula II; and 2) introducing an olefin into the reaction vessel, wherein at least two molecules of the olefin are coupled together.

The following examples illustrate the various embodiments of the present invention. All reactions are carried out in an inert, air-free atmosphere using vacuum line or dry box. All solvents are dry and deoxygenated. Those skilled in the art will recognize many variations that are within the spirit of the present invention and scope of the claims.

EXAMPLE 1

Reaction of (dimethoxyethane)NiBr$_2$+3,4-diaminotoluene in Water:

Approximately, 0.158 g (0.0013 mmol) of 3,4-diaminotoluene and 10 mL deoxygenated water are added to about 0.400 g (0.00130 mol) of (dimethoxyethane)NiBr$_2$. The resulting mixture is heated in a 110° C. oil bath for two hours. After cooling, 20 mL water, 3 mL concentrated ammonia, and a threefold excess of sodium hexafluorophosphate (0.655 g in 5 mL water) are added. The mixture turns purple immediately. The purple mixture is stirred for 64 hr at room temperature, during which time a dark purple solid forms slowly. The mixture is filtered to yield a colorless filtrate and the dark solid. The solid is washed with distilled water, then with methanol, and dried under vacuum. A blue solid is obtained (0.44 g).

The blue solid is subjected to the following polymerization testing. A sample of the blue solid is added to a 1-L stainless-steel pressure vessel containing isobutane (500 mL) and methylaluminoxane (MMAO)/heptane solution (1.0 mL of 6.7% MMAO). MMAO is a modified methylalumoxane available from Akzo-Nobel. Ethylene is fed on demand to maintain a constant pressure in the reactor. After 30 min., ethylene uptake is recorded, and the reactor is vented. The results of the polymerization test at various initial temperature is provided in table I. The testing indicates ethylene uptake but no production of solid polymer product. At 40° C., 23 g of ethylene was consumed, which calculates to an activity of 784 kg/(g Ni*hr).

TABLE I

| TEMPERATURE (° C.) | ETHYLENE CONCENTRATION (mol %) | CATALYST ACTIVITY (g/(g Ni*hr)) |
| --- | --- | --- |
| 40 | 25 | 784 |
| 60 | 25 | 136 |
| 80 | 25 | 68 |

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A catalyst comprising a complex having formula I:

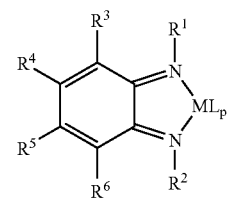

where

M is a metal selected from Groups 3 to 10 of the Periodic Table;

$R^1$ and $R^2$ are the same or different and are independently selected from hydrogen, $C_{1-10}$ alkyl, $C_{6-10}$ aryl, or $C_{7-15}$ aralkyl, each of these optionally substituted with halogen, cyano, $C_{1-4}$ alkoxy, or $C_{1-4}$ alkyl, and with the proviso that not more than 1 of $R^1$ or $R^2$ is a hydrocarbon which is branched at the imino-bonded carbon atom;

$R^3$, $R^4$, $R^5$, and $R^6$ are independently hydrogen, $C_{1-10}$ alkyl, $C_{6-10}$ aryl, $C_{7-15}$ aralkyl, $C_{1-10}$ alkoxy, or $C_{1-10}$ dialkylamino, each of these optionally substituted with halogen, cyano, $C_{1-4}$ alkoxy, or $C_{1-4}$ alkyl, or wherein any two adjacent $R^3$ through $R^6$ form a cyclic structure or are part of a larger ring structure, said cyclic structure and said larger ring structure optionally containing one or more heteroatoms, preferably B, N, O, S, or P;

L is a neutral or charged ligand; and p is a integer such that complex I is neutral and the valency of M is satisfied.

2. The catalyst of claim 1 wherein M is a metal from Groups 8 to 10 of the Periodic Table.

3. The catalyst of claim 1 wherein M is selected from the group consisting of nickel, palladium, iron, and cobalt.

4. The catalyst of claim 1 wherein L is a charged ligand selected from the group consisting of unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, boraaryl, and mixtures thereof.

5. The catalyst of claim 1 wherein L is a neutral ligand selected from the group consisting of carbonyl, $\eta^6$-aryl, $\eta^4$-butadiene, $\eta^4$-cyclobutadiene, $\eta^4$-cyclooctatetraene, tertiary phosphine, and mixtures thereof.

6. The catalyst of claim 1 wherein $R^1$ and $R^2$ are both hydrogen.

7. The catalyst of claim 1 having formula II:

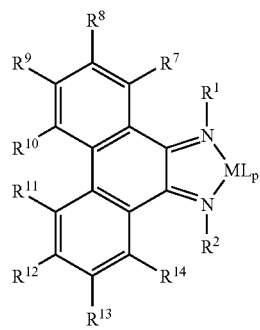

II where

M is a metal selected from Groups 3 to 10 of the Periodic Table;

$R^1$ and $R^2$ are the same or different and are independently selected from hydrogen, $C_{1-10}$ alkyl, $C_{6-10}$ aryl, or $C_{7-15}$ aralkyl, each of these optionally substituted with halogen, cyano, $C_{1-4}$ alkoxy, or $C_{1-4}$ alkyl, and with the proviso that not more than 1 of $R^1$ or $R^2$ is a hydrocarbon which is branched at the imino-bonded carbon atom;

$R^7$, $R^8$, $R^9$, $R^{10}$, $R^{11}$, $R^{12}$, $R^{13}$, and $R^{14}$ are independently hydrogen, $C_{1-10}$ alkyl, $C_{6-10}$ aryl, $C_{7-15}$ aralkyl, $C_{1-10}$ alkoxy, or $C_{1-10}$ dialkylamino, each of these optionally substituted with halogen, cyano, $C_{1-4}$ alkoxy, or $C_{1-4}$ alkyl, or wherein any two of $R^7$ through $R^{14}$, or $R^{10}$ and $R^{11}$ form a cyclic structure or are part of a larger ring structure, said cyclic structure and said larger ring structure optionally containing one or more heteroatoms, preferably B, N, O, S, or P;

L is a neutral or charged ligand; and p is a integer such that complex I is neutral and the valency of M is satisfied.

8. The catalyst of claim 1 further comprising an activator.

9. The catalyst of claim 8 wherein the activator is selected from the group consisting of alumoxanes, alkylaluminum compounds, and mixtures thereof.

10. The catalyst of claim 8 wherein the activator is an acid salt containing non-nucleophilic anions.

11. The catalyst of claim 8 wherein the activator is selected from the group consisting of lithium tetrakis(pentafluorophenyl) borate, lithium tetrakis(pentafluorophenyl) aluminate, anilinium tetrakis(pentafluorophenyl) borate, and mixtures thereof.

12. A process for coupling two or more olefins, the process comprising:

1) introducing into a reaction vessel an activator and a catalyst of formula I:

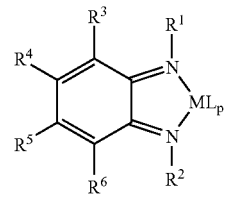

I where

M is a metal selected from Groups 3 to 10 of the Periodic Table;

$R^1$ and $R^2$ are the same or different and are independently selected from hydrogen, $C_{1-10}$ alkyl, $C_{6-10}$ aryl, or $C_{7-15}$ aralkyl, each of these optionally substituted with halogen, cyano, $C_{1-4}$ alkoxy, or $C_{1-4}$ alkyl, and with the proviso that not more than 1 of $R^1$ or $R^2$ is a hydrocarbon which is branched at the imino-bonded carbon atom;

$R^3$, $R^4$, $R^5$, and $R^6$ are independently hydrogen, $C_{1-10}$ alkyl, $C_{6-10}$ aryl, $C_{7-15}$ aralkyl, $C_{1-10}$ alkoxy, or $C_{1-10}$ dialkylamino, each of these optionally substituted with halogen, cyano, $C_{1-4}$ alkoxy, or $C_{1-4}$ alkyl, or wherein any two adjacent $R^3$ through $R^6$ form a cyclic structure or are part of a larger ring structure, said cyclic structure and said larger ring structure optionally containing one or more heteroatoms, preferably B, N, O, S, or P;

L is a neutral or charged ligand; and p is a integer such that complex I is neutral and the valency of M is satisfied; and 2) introducing at least one olefin into the reaction vessel, wherein at least two molecules of olefin are coupled together.

13. process of claim 12 wherein M is a metal from Groups 8 to 10 of the Periodic Table.

14. The process of claim 12 wherein M is selected from the group consisting of nickel, palladium, iron, and cobalt.

15. The process of claim 12 wherein L is a charged ligand selected from the group consisting of unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, boraaryl, and mixtures thereof.

16. The process of claim 12 wherein L is a neutral ligand selected from the group consisting of carbonyl, $\eta^6$-aryl, $\eta^4$-butadiene, $\eta^4$-cyclobutadiene, $\eta^4$-cyclooctatetraene, tertiary phosphine, and mixtures thereof.

17. The process of claim 12 wherein the activator is selected from the group consisting of alumoxanes, alkylaluminum compounds, and mixtures thereof.

18. The process of claim 12 wherein the activator is an acid salt containing non-nucleophilic anions.

19. The process of claim 12 wherein the activator is selected from the group consisting of lithium tetrakis(pentafluorophenyl) borate, lithium tetrakis(pentafluorophenyl) aluminate, anilinium tetrakis(pentafluorophenyl) borate, and mixtures thereof.

20. The process of claim 12 wherein said catalyst has the formula:

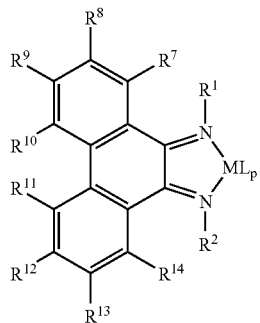

where
- M is a metal selected from Groups 3 to 10 of the Periodic Table;
- $R^1$ and $R^2$ are the same or different and are independently selected from hydrogen, $C_{1-10}$ alkyl, $C_{6-10}$ aryl, or $C_{7-15}$ aralkyl, each of these optionally substituted with halogen, cyano, $C_{1-4}$ alkoxy, or $C_{1-4}$ alkyl, and with the proviso that not more than 1 of $R^1$ or $R^2$ is a hydrocarbon which is branched at the imino-bonded carbon atom;
- $R^3$, $R^4$, $R^5$, and $R^6$ are independently hydrogen, $C_{1-10}$ alkyl, $C_{6-10}$ aryl, $C_{7-15}$ aralkyl, $C_{1-10}$ alkoxy, or $C_{1-10}$ dialkylamino, each of these optionally substituted with halogen, cyano, $C_{1-4}$ alkoxy, or $C_{1-4}$ alkyl, or wherein any two of $R^7$ through $R^{14}$, or $R^{10}$ and $R^{11}$ form a cyclic structure or are part of a larger ring structure, said cyclic structure and said larger ring structure optionally containing one or more heteroatoms, preferably B, N, O, S, or P;
- L is a neutral or charged ligand; and
- p is a integer such that complex I is neutral and the valency of M is satisfied.

* * * * *